United States Patent [19]

Vautrain

[11] 4,162,272

[45] Jul. 24, 1979

[54] SAFER PRODUCTION OF DRY LIQUID PROPANE SUBSTANTIALLY FREE FROM HF AND ORGANIC FLUORIDE

[75] Inventor: Lucien H. Vautrain, Sweeny, Tex.

[73] Assignee: Phillips Petroleum Company, Bartlesville, Okla.

[21] Appl. No.: 868,363

[22] Filed: Jan. 10, 1978

[51] Int. Cl.$^2$ .............................. C07C 9/14
[52] U.S. Cl. .......................... 62/24; 62/28; 585/719; 585/802; 585/854
[58] Field of Search .......... 260/676 R, 683.41, 683.42, 260/683.48; 210/71; 208/206

[56] References Cited

U.S. PATENT DOCUMENTS

| | | | |
|---|---|---|---|
| 2,463,076 | 3/1949 | Zimmerman et al. | 260/683.42 |
| 2,773,920 | 12/1956 | Vautrain et al. | 260/683.41 |
| 3,449,239 | 6/1969 | Moore | 208/206 |
| 3,542,196 | 11/1970 | Madlung, Jr. | 210/71 |
| 3,699,209 | 10/1972 | Ward | 260/683.41 |
| 3,919,342 | 11/1975 | Chapman | 260/683.48 |

Primary Examiner—George Crasanakis

[57] ABSTRACT

A dry liquid propane substantially free from HF, organic fluorides and water is produced by bringing into intimate contact with a sodium hydroxide solution containing not more than about 5 percent by weight NaOH a liquid propane stream obtained by heating a stream of the propane containing organic fluoride and bringing said stream in contact with a defluorinating agent, e.g., aluminum fluoride, to produce a stream of propane containing HF, the stream of propane containing organic fluorides having been obtained from a hydrogen fluoride stripper operated in conjunction with a depropanizing zone wherein an HF alkylation hydrocarbon product stream or effluent is depropanized. In an embodiment only a relatively small volume of propane containing HF is contacted with the aqueous sodium hydroxide solution whereupon the intermingled fluids are immediately passed into a body of settling propane and aqueous sodium hydroxide solution in a settling zone or vessel.

4 Claims, 1 Drawing Figure

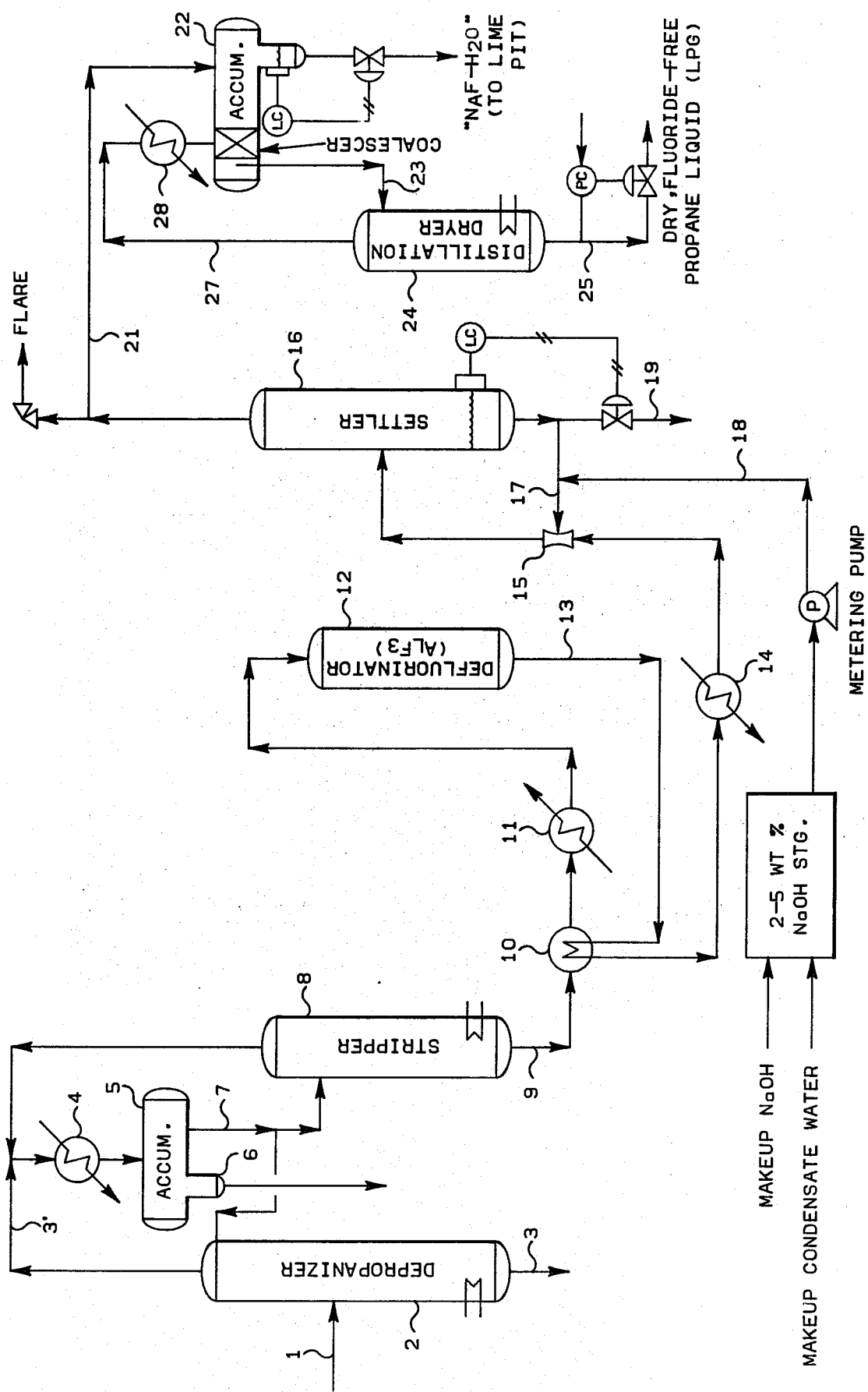

SAFER PRODUCTION OF DRY LIQUID PROPANE SUBSTANTIALLY FREE FROM HF AND ORGANIC FLUORIDE

This invention relates to the production of a dry propane liquid (LPG). In one of its aspects it relates to the treatment of a liquid propane stream containing hydrogen fluoride. In another of its aspects, it relates to a manner of contacting such a stream with a neutralizing fluid to neutralize the HF.

In one of its concepts the invention provides in a combination depropanizing, stripping, and defluorinating operation, in which organic fluorides in a propane stream have been converted to a propane stream containing hydrogen fluoride and organic compounds such as propylene, a neutralizing or contacting step in which a relatively small volume of liquid propane containing HF is contracted with an aqueous solution of sodium hydroxide, preferably not containing more than about 5 percent by weight NaOH, and then immediately passed into a body of settling propane and aqueous sodium hydroxide solution which is settling in a settling zone, recovering propane from the settling zone and subjecting the propane to a drying operation, e.g., a distillation-drying operation in which an overhead of sodium fluoride in water is recovered and disposed of as desired as by sending it to a lime [aqueous $Ca(OH)_2$]pit, while bottoms from the distillation are removed as a dry, fluoride-free propane liquid (LPG). In another of its concepts in a combination operation as just described there is provided an eduction or intimate contacting and mixing section or zone operated in conjunction with a settling zone or settler, caustic solution being circulated from said settler to said eduction zone or eductor and therein admixing with liquid propane containing HF flowing from a defluorinating zone to said settler whereupon the admixed liquid propane and caustic solution is passed to said settling zone for recovery of propane as earlier described and as further described herein.

In the type of operation herein described there has been employed a neutralization of HF contained in liquid propane in which for the neutralization step solids lumps of KOH which are self-cleaning, have been used. Solid KOH has the property of sloughing off the reaction product of HF and KOH as it is formed so that a fresh surface is always presented to the fluid entering the neutralizing zone or section.

The operation using solid KOH, just described, works very well. However, an explosion and fire have been experienced when there has occurred a sudden surge in the flow of liquid HF in the HF-containing liquid propane entering the solid KOH treating vessel. This explosion has been attributed to the sudden heat evolved by the reaction of HF with KOH and the heat generated was absorbed by the liquid propane. This heat evolved caused the liquid propane to vaporize. This resulted in an undue pressure increase causing the explosion and fire.

It is, of course, desirable to eliminate as far as possible all hazards or dangers which are observed.

The present invention positively precludes any possible explosion and fire by virtue of its essential design and operation.

It is an object of this invention to produce safely a liquid propane free from HF, organic fluorides and water. It is another object of this invention to produce such a stream in a safe manner. It is a further object of this invention to provide a combination of steps for producing a substantially pure, dry liquid propane stream freed from hydrogen fluoride and water albeit the raw material for the production of such a stream is taken from an HF alkylation operation, more specifically, from a combination depropanizer and HF stripping operation.

Other aspects, concepts, objects and the several advantages of this invention are apparent from a study of this disclosure, the drawing and the appended claims.

According to the present invention, a propane liquid substantially free from organic fluorides, hydrogen fluoride and water is produced in a process comprising the steps as follow: obtaining a stream of propane from a depropanizing zone wherein a hydrocarbon stream containing propane is fractionated to obtain said propane stream, passing the propane-containing stream to an HF stripping zone, and in said zone stripping HF from said propane stream, heating the now substantially free-from-HF propane stream to a temperature at which organic fluorides contained therein will be decomposed, as with aluminum fluoride, in a defluorinating zone, passing the said stream to a defluorinating zone, in said defluorinating zone decomposing organic fluorides to form HF and organic compounds, e.g., propylene, in said propane stream, now cooling said propane stream and passing it substantially as a liquid containing hydrogen fluoride into contact with an aqueous sodium hydroxide solution at a concentration of not over about 5 percent by weight NaOH, in said contact neutralizing hydrogen fluoride, forming sodium fluoride, allowing the admixed propane and aqueous solution to settle, recovering a liquid propane phase and drying said propane phase to obtain said dry propane liquid substantially free from HF, organic fluorides and water.

Also according to the present invention, there is provided in the process described a contacting of a flowing stream of liquid propane containing HF with a flowing stream of the aqueous sodium hydroxide solution in a mixing section or zone the total volume of which is relatively small compared with the volume of the zone in which the settling of the two phases takes place.

Still further according to the invention, the contacting is accomplished in an eductor or equivalent section or zone.

Referring now to the drawing, a desired propane-containing feed 1, e.g., an isobutane-propane stream fractionated from an HF alkylation hydrocarbon product or a portion of the total hydrocarbon alkylation hydrocarbon, is charged to a depropanizer 2. Bottoms containing isobutane and heavier is removed for further conventional fractionation at 3, for example, to recover isobutane for recycle, to recover alkylate product and normal butane.

Normally, the overhead from the propanizer 2 includes any propane added to the HF alkylation in the hydrocarbon feedstreams plus any propane produced during the HF alkylation of isobutane as with propylene-butylenes olefin feed. This propane must be removed from the system, i.e., not recycled because build up of propane in the HF alkylation process is undesirable. The overhead yield from the depropanizer 2 is passed by 3' into and through condenser 4 into accumulator 5, bottoms of which are taken from keg 6 as hydrogen fluoride which can be returned to the HF alkylation reaction. A liquid propane stream is passed by 7 into stripper 8 wherein HF is stripped from the propane under stripping conditions which include reboiling of the foot of the stripper column. Propane now substantially freed from HF but containing organic fluorides is passed by 9 heat exchanger 10 and heater 11 into defluorinator 12. The conditions in the defluorinator are such that the organic fluoride will be decomposed to organic compounds, such as propylene, and hydrogen fluoride. These conditions are known in the art. Bottoms from defluorinator 12 through 13 heat exchanger 10 and cooler 14 into eductor or injector 15 wherein the stream is mixed with a stream of aqueous sodium hydroxide solution taken from settler 16 by 17. As needed fresh sodium hydroxide solution can be introduced by 18. The volume of total liquid in settler 16 is considerably larger than that in eductor 15 as will be understood by one skilled in the art having studied this disclosure. The admixed liquids are passed to settler 16 wherein two phases are formed. The bottom phase is cycled to the eductor. A small portion of reagent can be removed periodically or continuously from the circulation system by 19 and replaced by fresh solution coming in through 18. The discarded reagent can be sent to a lime pit. A liquid propane phase settling on top of the aqueous sodium hydroxide solution in settler 16 is taken overhead by 21 into accumulator 22. From accumulator 22 there is removed an aqueous NaOH-sodium fluoride solution which can be disposed of as desired as to a lime pit. The propane phase is taken from accumulator 22 by 23 into distillation dryer 24 the bottom of which is heated or reboiled permitting withdrawal therefrom by 25 of a dry, fluoride-free propane liquid (LPG). Overhead from the distillation dryer is passed by 27 and condenser 28 into accumulator 22.

It will be seen that in the eductor while there is a fairly rapid volume flow of propane liquid relative to the caustic solution, i.e. the flow may be anywhere from 4:1 to 20:1, the values given are approximate, there is at any one time only a small volume of propane liquid involved, i.e., that volume which can be contained in the eductor and accordingly, any surge of propane containing HF or any surge in HF in the propane liquid which would tend to evolve a large quantity of heat can be dealt with effectively without explosion.

In the table there is given a calculated example with ranges and specific operating parameters or conditions.

One skilled in the art having studied this disclosure will recognize the changes which he may wish to make for any particular feedstocks, solutions, etc.

Table

| (I) Operating Conditions: | Specific |
|---|---|
| (12) AlF$_3$ Defluorinator: | |
| Pressure, psig., | |
| Range 280 to 310 | 300 |
| Temperature, °F., | |
| Range 350 to 400 | 375 |
| Contact Time, seconds, | |
| Range 2 to 10 | 5 |
| (16) Settler and Eductor (15): | |
| Pressure, psig., | |
| Range 275 to 305 | 295 |
| Temperature, °F., | |
| Range 100 to 150 | 125 |
| Volume Ratio Propane/Caustic Solution Mixed in Eductor (15), | |
| Range 4:1 to 20:1 | 10:1 |
| Volume Ratio Propane/Caustic Solution in Settler (16) | |
| Range 5:1 to 30:1 | 15:1 |
| (24) Distillation-Dryer: | |
| Top of Unit, | |
| Pressure, psig., | |

Table-continued

| | |
|---|---|
| Range 225 to 275 | 265 |
| Temperature, °F., | |
| Range 120 to 135 | 127 |
| Bottom of Unit, | |
| Pressure, psig., | |
| Range 275 to 295 | 285 |
| Temperature, °F., | |
| Range 133 to 150 | 135 |
| (22) Accumulator (with Coalescer): | |
| Pressure, psig., | |
| Range 250 to 270 | 260 |
| Temperature, °F., | |
| Range 80 to 130 | 100 |
| (II) Stream Flows: | |
| (9) Feed to Defluorinator (12): | |
| Volume, barrels/hr., [a] | 9 |
| Composition [b], vol. % [c] | |
| Propane, | 99.25 |
| Isobutane | 0.75 |
| Organic fluorides, ppm. by wt. [d], | 25 |
| HF, ppm. by wt. [d], | 10 |
| (13) Yield from (12), Feed to (16): | |
| Volume, barrels/hr. [a], | 9 |
| Composition [b], vol. % [c], | |
| Propane, | 99.25 |
| Isobutane, | 0.75 |
| Organic fluorides, ppm. by wt. [d], | nil |
| HF, ppm. by wt. [d], | 18 [e] |
| (17) Aqueous NaOH Solution: | [f] |
| NaOH, wt. %, | |
| Range 2 to 5 [g] | 3 |
| Propane/Caustic Solution, vol. ratio in Settler (16), | |
| Range 5:1 to 30:1 | 15:1 [h] |
| (21) Propane from Settler (16), [i] | |
| Volume, barrels/hr., [a], | 9 |
| Composition [b], vol. % [c], | |
| Propane, | 99.25 |
| Isobutane, | 0.75 |
| Organic fluorides, ppm. by wt. [j], | nil |
| HF, ppm by wt. [j], | nil |
| (25) Propane (LPG) Yield: | |
| Volume, barrels/hr., [a] | 9 |
| Composition [b], vol. % [c], | |
| Propane, | 99.25 |
| Isobutane, | 0.75 |
| Organic fluorides, ppm. by wt., | nil |
| HF, ppm. by wt., | nil |
| H$_2$O, ppm. by wt., | nil |

[a] Volume can vary from 0 to 50 barrels/hr., or more, depending upon operation;
[b] Can vary, depending upon plant operation;
[c] Except as noted;
[d] Parts per million by weight can vary from <1 to 50 on HF and on organic fluorides. Can be much higher than 50 ppm. during upsets;
[e] Propyl fluoride being broken down to HF and propylene;
[f] 200 lb. batch of caustic solution in settler (16), made with steam condensate to eliminate any solids formation from CaF$_2$, etc.;
[g] Maximum is about 5 wt. % NaOH to prevent any precipitation of NaF from the solution;
[h] In eductor or injector (15) the propane/caustic solution volume ratio can range from about 4:1 to about 20:1, specifically about 10:1;
[i] Contains "moisture" from settler (16);
[j] Can be considerable during upsets, but the aqueous NaOH can absorb such heat of reaction of HF with NaOH to prevent explosions due to high temperature effects on liquid propane which is about at its bubble point.

Reasonable variation and modification are possible within the scope of the foregoing disclosure, drawing, and appended claims to the invention the essence of which is that a safe process for the removal of HF from propane containing the same has been provided wherein, essentially, the total volume of propane and caustic solution is maintained relatively small respecting the volume of propane and caustic solution in a settler to which the admixed propane containing HF and caustic solution is passed for settling, the rates of flow of the fluids being contacted being adjustable as desired thus to accommodate any surges of excessive quantities of HF and therefore generation of heat thus to avoid explosions.

What is claimed is:

1. A process for the production of a liquid propane substantially free from organic fluoride, hydrogen fluoride and water, in a safe manner, the steps which comprise obtaining a stream of propane in a depropanizing zone wherein a hydrocarbon stream containing propane is fractionated to obtain said propane stream, passing the propane-containing stream to an HF stripping zone to strip HF from said propane stream, heating the liquid propane stream separated from said HF stripping zone to a temperature at which organic fluorides contained therein can be decomposed in a defluorinating zone, containing aluminum fluoride, passing said heated propane stream to said defluorinating zone, to break up organic fluorides to form HF in said propane stream, cooling said defluorinated propane stream and passing same into a mixing section, which is relatively small compared with the volume of a settling zone in which the phases are to be settled and separated, into a contact with a flowing stream of aqueous sodium hydroxide solution having a concentration of not over about 5 percent by weight sodium hydroxide to neutralize hydrogen fluoride, forming sodium fluoride, and immediately passing the thus contacted mixture into said settling zone, recovering from said settling zone a propane phase and drying said propane phase to obtain said liquid propane substantially free from HF, organic fluorides and water.

2. A process according to claim 1 wherein said mixing section comprises an eductor.

3. A process according to claim 1 wherein the flow of propane liquid being contacted with the aqueous sodium hydroxide solution is in the ratio 4:1 to 20:1.

4. A process according to claim 3 wherein the contact of the flowing fluids is accomplished in an eductor.

* * * * *